United States Patent [19]
Yeh

[11] Patent Number: 6,059,756
[45] Date of Patent: May 9, 2000

[54] SAFETY INJECTION DEVICE

[76] Inventor: Song-Hwa Yeh, 3Fl.-2, No. 406, Wanta Rd., Tiapei, Taiwan

[21] Appl. No.: 09/186,344

[22] Filed: Nov. 4, 1998

[51] Int. Cl.[7] ...................................................... A61M 5/00
[52] U.S. Cl. ............................................ 604/218; 604/195
[58] Field of Search ..................................... 604/110, 187, 604/195, 218, 198, 263

[56] References Cited

U.S. PATENT DOCUMENTS

| | | |
|---|---|---|
| 4,826,491 | 5/1989 | Schramm . |
| 4,943,282 | 7/1990 | Page et al. . |
| 5,057,087 | 10/1991 | Harmon . |
| 5,059,185 | 10/1991 | Ryan . |
| 5,222,947 | 6/1993 | D'Amico . |
| 5,304,149 | 4/1994 | Morigi . |
| 5,344,403 | 9/1994 | Lee ........................................... 604/110 |
| 5,458,576 | 10/1995 | Haber et al. ............................. 604/110 |
| 5,843,047 | 12/1998 | Pyrozyk et al. . |

FOREIGN PATENT DOCUMENTS 8803 216 U   10/1988   Germany .

OTHER PUBLICATIONS

Becton–Dickinson Brochure 1995.
Safety Syringes A 'Hot Zone', *Investment Report*, Summer 1996.
Sketch of Monoject device obtained at a show in New York, Jun. 2, 1997.

*Primary Examiner*—John D. Yasko
*Attorney, Agent, or Firm*—Kolisch, Hartwell, Dickinson, McCormack & Heuser

[57] ABSTRACT

A safety injection device has a barrel, a seat operatively and slidably received within the barrel and having a needle cannula extending out therefrom, a stopper detachably received in a chamber defined in the seat and a plunger slidably received in the barrel and having a pair of connectors detachably received in the stopper and a pair of spaced extensions The gap between the two extensions allows the plunger to engage with the stopper and therefore to push the seat originally received in the barrel. Due to the movement of the connectors, the seat is able to be secured with respect to the barrel with the needle cannula extending out from the barrel and pulled back into the barrel with the needle cannula received in the barrel. With such a construction, human intervention in the disposal and exposure to the contaminated cannula is avoided, and therefore, the risk of infection is reduced.

11 Claims, 9 Drawing Sheets

SAFETY INJECTION DEVICE

BACKGROUND OF THE INVENTION

1. Field of the invention

The present invention relates to a safety injection device, and more particularly to a safety injection device having a plunger, a stopper adapted to be mated with the plunger and a seat movably received a barrel and having a needle cannula securely mounted thereto. The plunger together with the stopper is able to move the seat in the barrel to a first position where the seat is stationary and the needle cannula extends out from the locking tip of the barrel and a second position where the needle cannula is entirely received in the barrel, therefore, hazard of infection by the used needle cannula and even injury is avoided.

2. Background of the invention

Nurses, doctors or even environmental recyclists all treat hospital waste as extremely hazardous, especially radioactive waste and hypodermic needles. Radioactive waste is hazardous because of the radiation, and the hypodermic needles are hazardous because the contaminated cannulas can infect people with fatal diseases. To avoid injury and exposure to disease from used needles, attendants often use a small cap disengagably attached to the top of the barrel to enclose the sharp tip of the needle. However, during the process of placing the cap on the needle, people are exposed to germs and virus if the skin is inadvertently pierced. To prevent such a tragedy from happening, a safety device is introduced into the market, which enables people who takes care of the needle to dispose of the needles quickly and safely. The device is a box-like device with which a user is able to disengage the needle cannula from the barrel and securely hold the needle cannula therein, such that attendants will not think handling used needles is a frightening job. Indeed, the box-like safety device ensures the safety of the attendants, but it also causes another kind of pollution to the environment. The safety device is a separate part from the needle, which means that manufacturers will have to produce and store it separately. Furthermore, once the device is used, it cannot be recycled. It will be discarded, which increases the social burden to deal with the waste. Therefore, the invention intends to introduce a safety injection device to mitigate and/or obviate the aforementioned problems.

SUMMARY OF THE INVENTION

It is the main objective of the invention to introduce a safety injection device which a user is able to dispose of the used hypodermic needle directly without worrying that the needle might accidentally hurt someone.

A secondary objection of the invention is to provide a novel plunger which has two plate bodies each having a first end integrally formed therewith and a second end spaced apart from each other and having a head formed thereon. With such a constructed plunger, a seat with a needle cannula is able to be moved between a first position where the needle cannula is entirely received within the barrel and a second position where the needle cannula extends out from the locking tip of the barrel. Such that a hands-free safety injection device is achieved.

A further objective of the invention is to introduce a stopper having a plurality of slits defined therein, such that all of the liquid in the barrel is able to be ejected out completely.

Other novel features and advantages of the invention will become more apparent from the following detailed description when taken in conjunction with the accompanying drawings.

DETAILED DESCRIPTION OF THE PREFERRED EMBODIMENT

Figure 1:
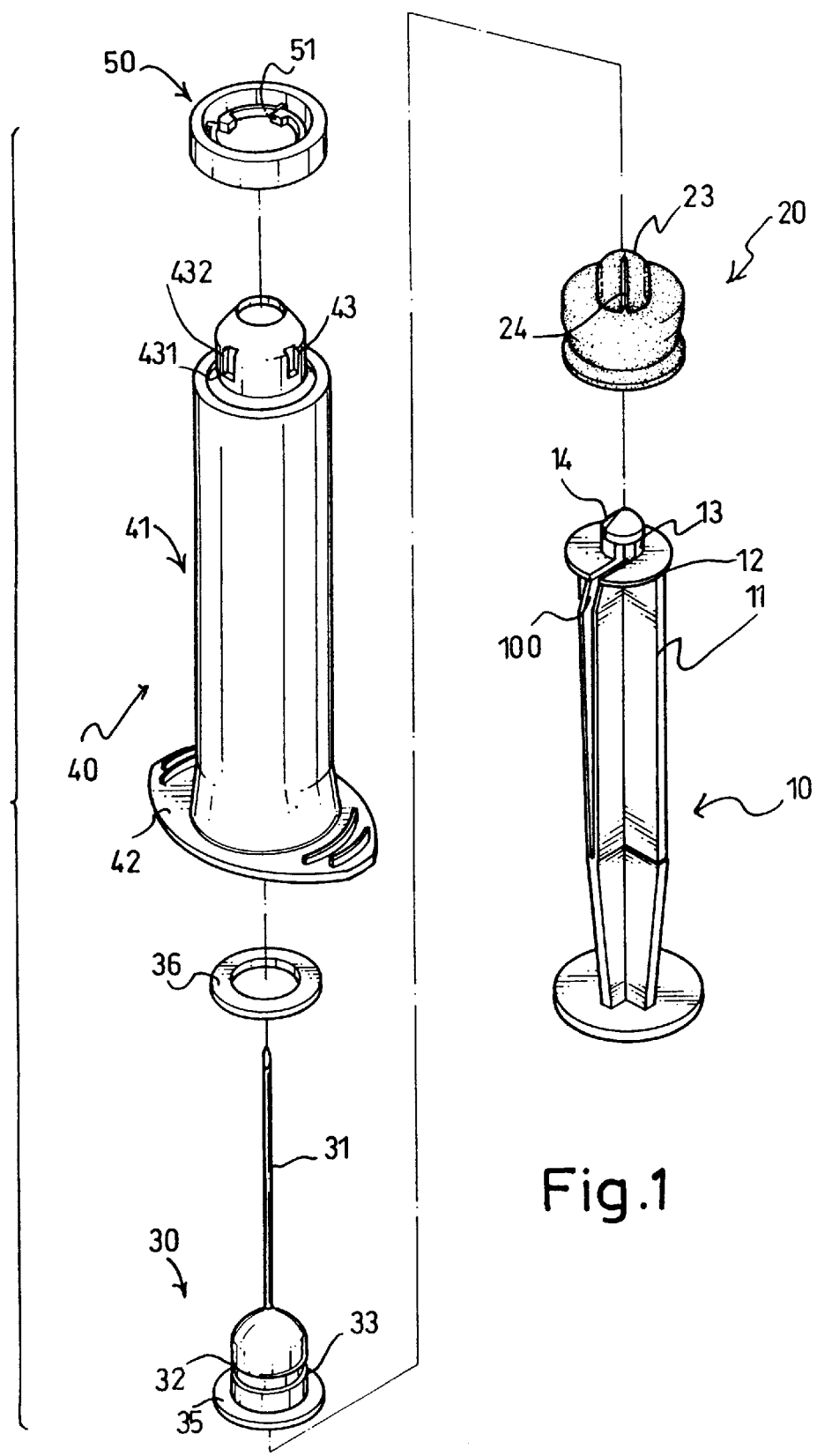
FIG. 1 is an exploded perspective view of a preferred embodiment of a safety injection device constructed in accordance with the present invention.
Figure 6:
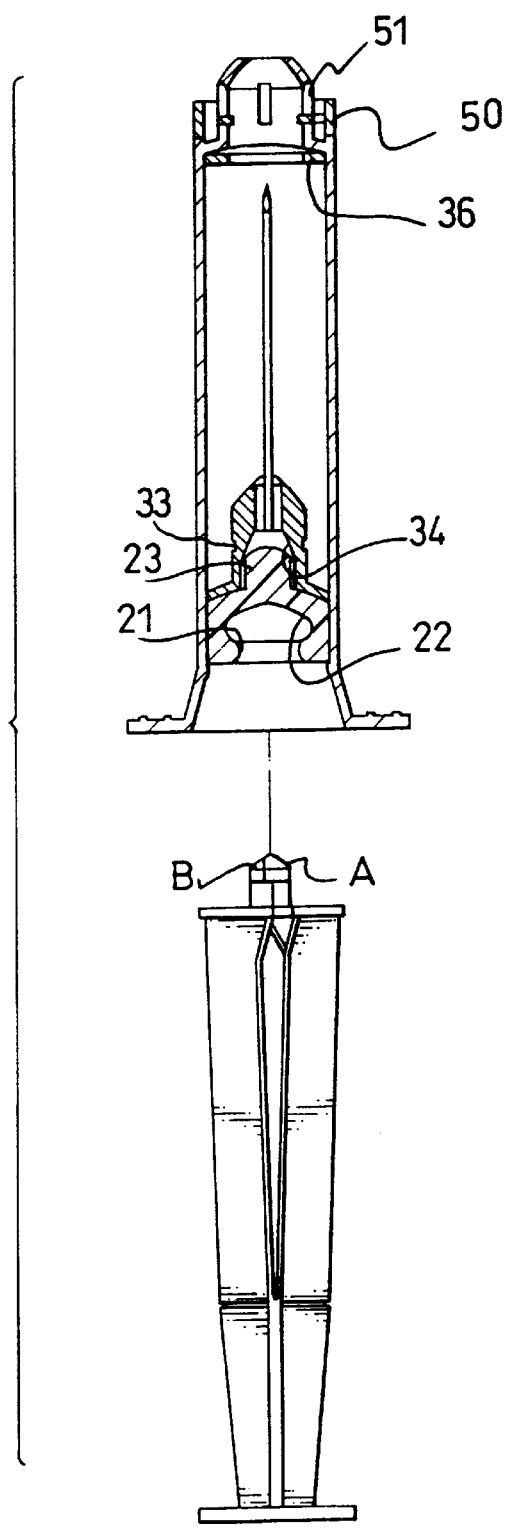
FIG. 6 is a schematic view showing the plunger, a barrel and a seat together with a stopper received in the barrel.

Referring to FIG. 1, a safety injection device of the invention comprises a plunger (10), a stopper (20) detachably connected with the plunger (10), a seat (30) having a chamber (34), as shown in FIG. 6, defined to detachably receiving a portion of the stopper (20) therein and a cannula (31) securely connected therewith, a barrel (41) slidably receiving the seat (30), the stopper (20) and the plunger (10) therein and a retainer (50) snappingly fitted with a locking tip (43) and disengagably connected with the seat (30).

The plunger (10) has two extensions (11) each having a first end securely connected with each other and a second end movably engaged with one another. Furthermore, the extensions (11) are spaced apart from each other by a gap (100). Each one of the second ends of the extensions (11) have a half-circular disk (12), a support (13) extending upright from the disk (12) and a connector (14) integrally formed on the free end of the support (13). Each of the connectors (14) is designed complementarily with respect to each other and in such a way that when the two connectors (14) are connected together, one of the connectors (14) is still movable in relation to the other and the gap (100) remains.

Referring to FIG. 6, the stopper (20) has a shoulder (21), a first chamber (22) defined for receiving the connectors (14) of the plunger (10) therein, and a nipple (23) formed therewith and having a plurality of slits (24) defined in the periphery thereof.

Referring to FIGS. 1 and 6, the seat (30) has a cannula (31) securely connected therewith, a body (32), an annular groove (33) defined in the outer face of the body (32), a second chamber (34) defined to detachably receive the nipple (23) of the stopper (20), a skirt (35) formed with the seat (30) and a water tight seal (36) seated onto the skirt (35). The barrel (41) has a finger flange (42) formed on one end thereof and the locking tip (43) is formed on the other end thereof. The locking tip (43) integrally formed on the barrel (41) has a plurality of through holes (431) defined around the face thereof and a plurality of elongate holes (432) each corresponding to one of the through holes (431) and defined as a guide. The retainer (50) is a hollow disk-like component. The retainer (50) has a plurality of protrusions (51) extending toward the center of the retainer (50) and each of the protrusions (51) corresponds to one of the elongate holes (432), such that when the retainer (50) is assembled with the locking tip (43) of the barrel (41), each of the protrusions (51) is able to slide along one of the corresponding elongate holes (432) and rest in the corresponding through hole (431).

Figure 2:
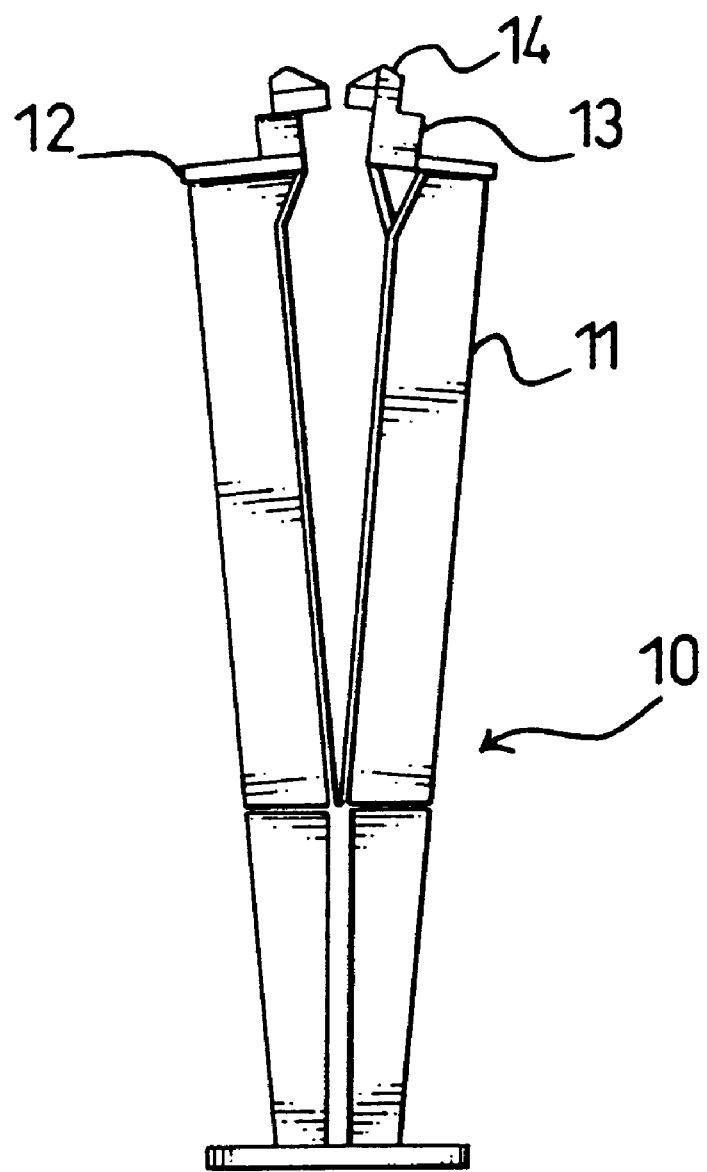
FIG. 2 is a plan view of a plunger as shown in FIG. 1 wherein two heads thereof are separate from each other.
Figure 3:
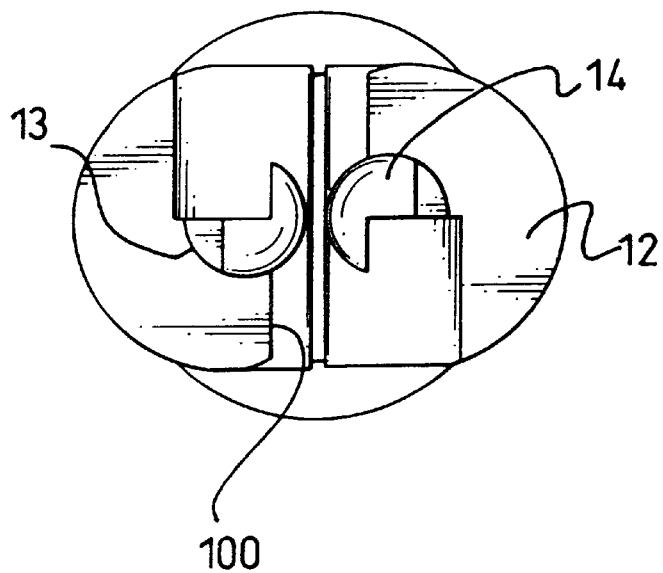
FIG. 3 is a top plan view of the plunger of FIG. 2.
Figure 5:
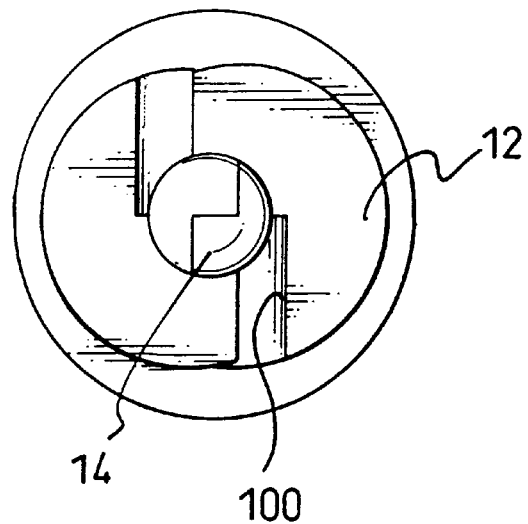
FIG. 5 is a top plan view of the plunger as shown in FIG. 1.
Figure 4:
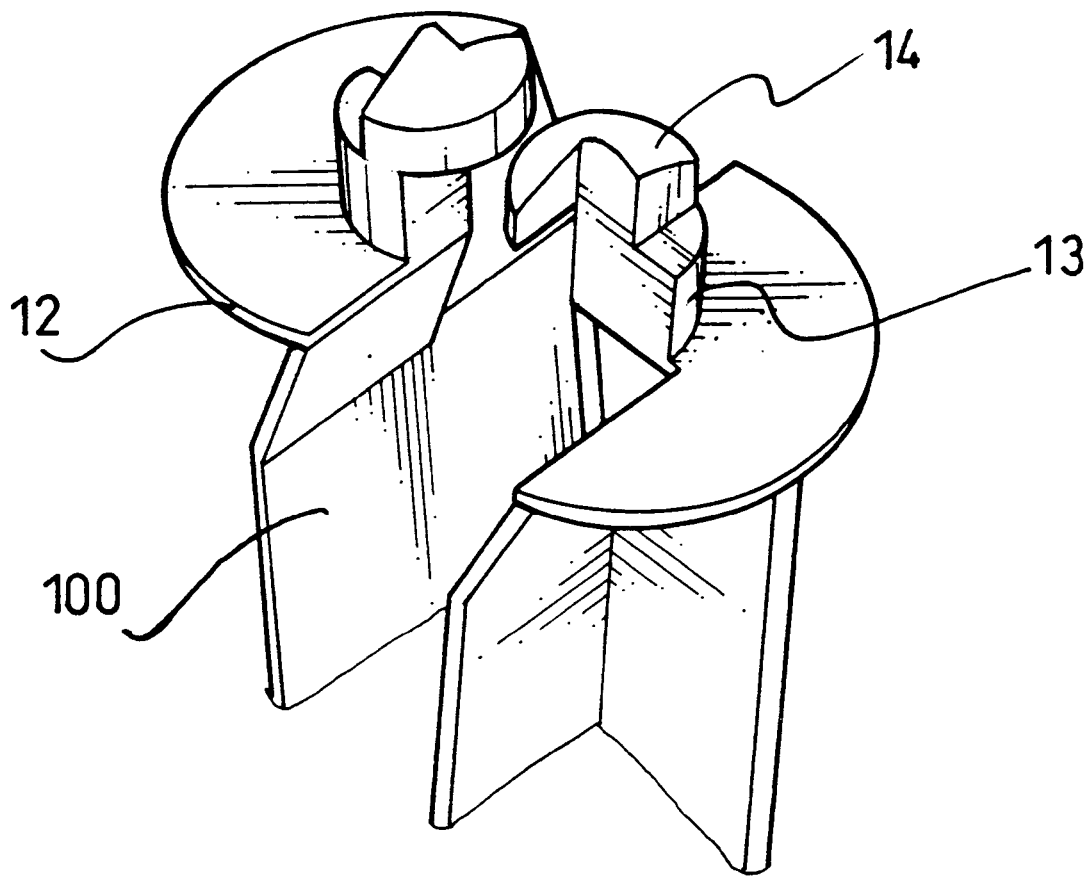
FIG. 4 is a partial perspective view of the plunger as shown in FIG. 2.

Referring to FIGS. 2 and 3, when the plunger (10) is produced, the extensions (11) and the connectors (14) are separate from each other and the gap (100') between the extensions (11) is greater than the gap (100) when the connectors (14) are connected together. The connectors (14), as mentioned before, are construed complimentarily with respect to each other and in a manner that when the connectors (14) are connected, each of the connectors (14) is movable in relation to the other, as shown in FIG. 5.

Figure 7:
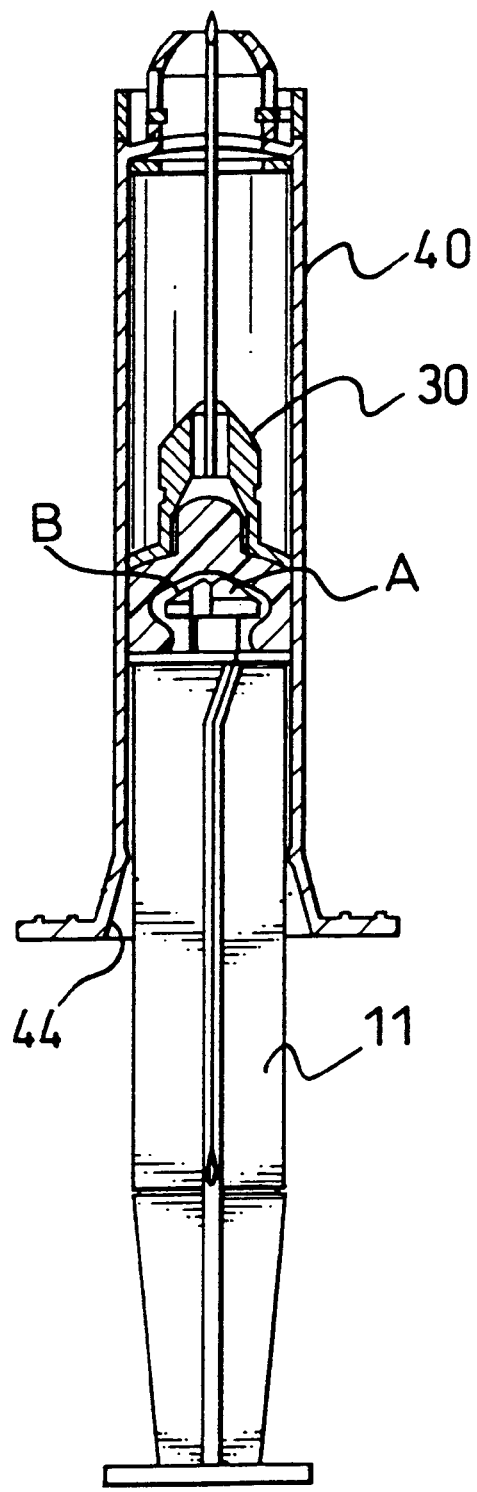
FIG. 7 shows a plan view of the assembly of the plunger with the stopper in the barrel.

Referring to FIGS. 1 and 6, the seat (30) and the stopper (20) are first accommodated within the barrel (40), wherein the cannula (31) is entirely received in the barrel (40) and the nipple (23) is received in the second chamber (34). Meanwhile, the connectors (14) of the plunger (10) are movably connected with respect to each other. For better understanding to the movement of the respect one of the connectors (14), the one on the right side in the drawing is labeled as A and the one on the left side in the drawing is labeled as B. Before the plunger (10) is inserted into the barrel (40), the diameter of the plunger (10) with the extensions (11) separated from each other is slightly greater than the diameter of the inner diameter of the barrel (40). When the plunger (10) is inserted into the barrel (40) as shown in FIG. 7, the two opposite edges of each of the disks (12) and the extensions (11) are forced to move toward each other by the inner surface of the barrel (40). The connector A on the right side will move further to the right and the connector B will move further to the left thereby spreading the overall diameter of the connector (A,B) and the first chamber (21) of the stopper (20) will then be held securely between the two connectors A and B. The gap (100) is tapered with the gap (100) near the disk (12) greater than the gap (100) near the joint of the extensions (11). Therefore, when the plunger (10) slides the stopper (20) and the seat (30) into the barrel (41), the pressing force of the inner surface of the barrel (41) on the extensions (11) reduces and the connector A and the connector B will gradually return to their original positions.

Figure 8:
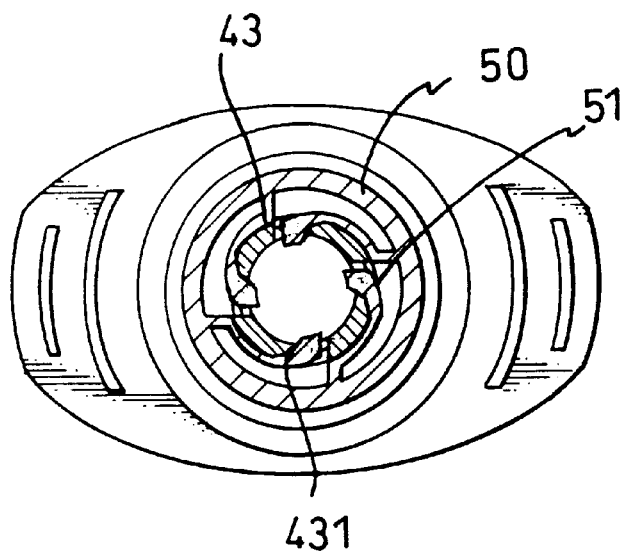
FIG. 8 is a schematic view showing the engagement between the seat and the locking tip of the barrel by means of a retainer.
Figure 10:
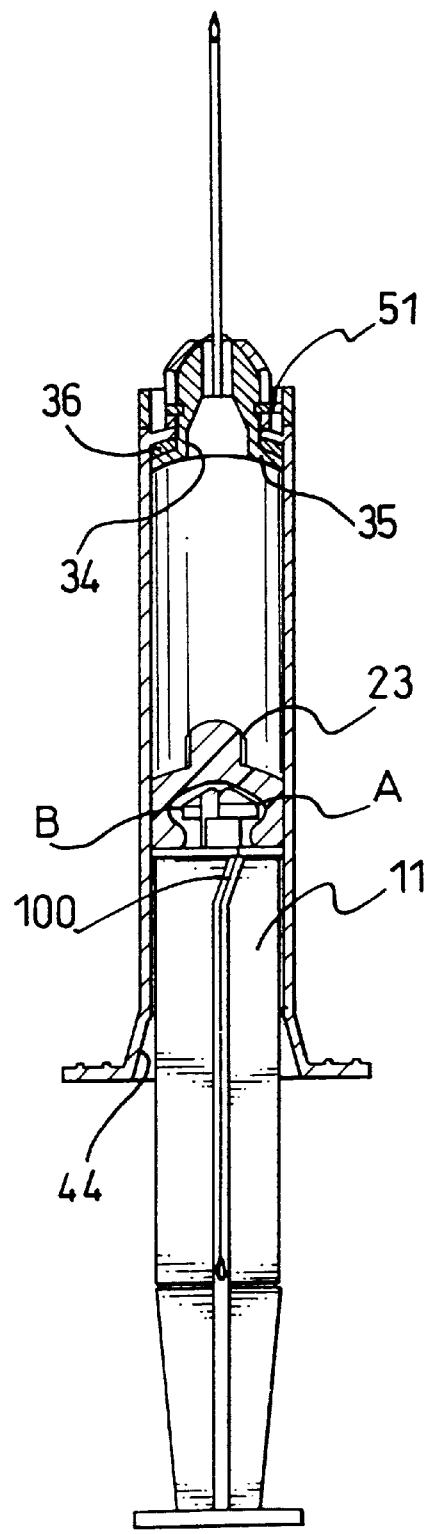
FIG. 10 shows a partial cross sectional plan view of the disengagement between the seat and the stopper together with the plunger.
Figure 11:
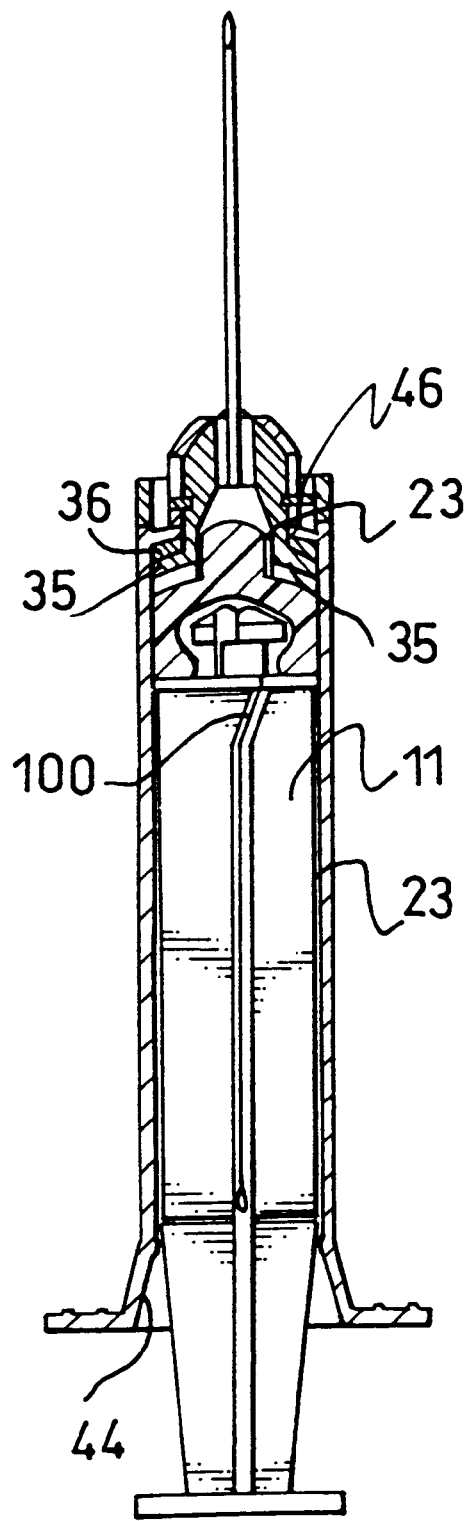
FIG. 11 is a schematic view showing the practical function of the slits of the stopper.

After the retainer (50) engages the locking tip (43) of the barrel (41) by the protrusions (51) with the corresponding through holes (431), as shown in FIG. 8, the seat (30) is secured by the protrusions (51) extending into the grooves (33). At the time that the seat (30) is secured by the extending protrusions (51), the plunger (10) is able to pull the stopper (20) back into the barrel (41) to have the hypodermic needle ready for use, as shown in FIG. 10, because the retaining force of the connectors (14) to the stopper (20) is greater than that of the nipple (23) and the second chamber (34) which is less than that of the protrusions (51) to the seat (30).

Figure 9:
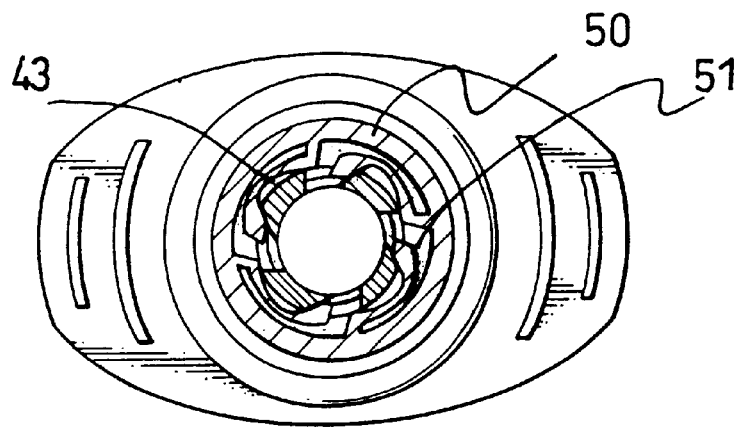
FIG. 9 is a top schematic view of the disengagement between the retainer with the locking tip.

As shown in FIG. 9, after the cannula (31) has been used, a user is able to rotate the retainer (50), either clockwise or counterclockwise, to force the protrusions (51) of the retainer (50) to retract and release the seat (30). When the seat (30) is free from the retainer (50), the user extends the plunger (10) into the barrel (41) to allow the nipple (23) of the stopper (20) to be accommodated in the second chamber (34). Afterwards, the seat (30) is able to be pulled back in the barrel (41) as shown in FIG. 7. As the stopper (20) moves toward the opening (44) in the barrel (41), the connectors (14) will gradually return to their original positions and release the stopper (20) because of the greater diameter of the opening (44) of the barrel (41).

By having the seat (30) with the cannula (31) pulled back to the inside of the barrel (40) by the action of the plunger (10), the risk of being injured or infected by the contaminated cannula (31) is greatly reduced.

Furthermore, in a conventional hypodermic needle, there is always remaining fluid between the stopper (20) and the bottom face of the skirt (35). To solve the problem, the provision of the slits (24) defined in the face of the nipple (23) enables the remaining fluid between the stopper (20) and the bottom face of the skirt (35) to flow out smoothly.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A safety injection device comprising:
   a barrel;
   a seat slidably received in the barrel and having a cannula selectively extending out from the seat, a body provided with a first chamber therein and an annular groove defined in the outer surface thereof, a skirt formed therewith and a seal securely located on the skirt and sealingly received in the barrel;
   a stopper having a nipple detachably received in the first chamber of the seat, a second chamber and a plurality of slits defined to communicate with the first chamber of the seat; and
   a plunger.

2. The device as claimed in claim 1, wherein the barrel further comprises a locking tip engaged with the body of the seat and having a plurality of through holes defined therethrough.

3. The device as claimed in claim 2, wherein the locking tip has a plurality of elongate holes each corresponding to one of the plurality of through holes.

4. The device as claimed in claim 3 further comprising a retainer having a plurality of protrusions each extending out from one of the corresponding through holes and slidably movable in a one of the corresponding elongate holes.

5. The device as claimed in claim 4, wherein each one of the protrusions engages with the groove of the body.

6. The device as claimed in claim 1, wherein the plunger has two extensions, the first ends of which respectively have a connector movably connected with respect to each other and detachably received in the second chamber.

7. The device as claimed in claim 6, wherein each of the extensions has a semicircular disk, a support extending out from the disk and a connector, wherein each connector is complementary in relation to each other.

8. The device as claimed in claim 7, wherein the movably engaged connectors are able to be inserted into the second chamber.

9. The device as claimed in claim 8, wherein a gap exists between the movably engaged connectors.

10. The device as claimed in claim 6 wherein the barrel has an opening with a diameter greater than the diameter of the engaged extensions and the disks.

11. The device as claimed in claim 10, wherein the barrel has a diameter smaller than the diameter of the opening, but greater than the engaged disks.

* * * * *